(12) United States Patent
Cheon et al.

(10) Patent No.: US 11,628,095 B2
(45) Date of Patent: Apr. 18, 2023

(54) CAST FOR PROTECTING AFFECTED AREA OF PATIENT

(71) Applicant: New Cast Industry Co., Ltd., Ulsan (KR)

(72) Inventors: Byeong Su Cheon, Ulsan (KR); Sang Soo Lee, Ulsan (KR)

(73) Assignee: NEW CAST INDUSTRY CO., LTD.

( * ) Notice: Subject to any disclaimer, the term of this patent is extended or adjusted under 35 U.S.C. 154(b) by 133 days.

(21) Appl. No.: 17/114,727

(22) Filed: Dec. 8, 2020

(65) Prior Publication Data

US 2021/0275360 A1 Sep. 9, 2021

(30) Foreign Application Priority Data

Mar. 9, 2020 (KR) ........................ 10-2020-0029014

(51) Int. Cl.
*A61F 13/04* (2006.01)
*A61F 13/00* (2006.01)
*A61L 15/12* (2006.01)

(52) U.S. Cl.
CPC ........ *A61F 13/04* (2013.01); *A61F 13/00987* (2013.01); *A61L 15/125* (2013.01)

(58) Field of Classification Search
CPC .. A61F 13/04; A61F 13/00987; A61F 13/104; A61F 13/041; A61F 13/046; A61F 13/06; A61F 13/064; A61F 13/066; A61F 13/10; A61F 13/107; A61L 15/125; A61L 15/07; A61L 15/08; A61L 15/10; A61L 15/12; A61L 15/14

See application file for complete search history.

(56) References Cited

U.S. PATENT DOCUMENTS

| | | | | |
|---|---|---|---|---|
| 5,256,134 A | * | 10/1993 | Ingham | A61F 13/04 602/8 |
| 5,403,267 A | * | 4/1995 | Pearce | D04B 21/18 602/76 |
| 5,409,448 A | * | 4/1995 | Kelley | A61F 13/04 602/8 |
| 5,514,080 A | * | 5/1996 | Blott | A61F 13/046 602/8 |
| 10,500,101 B1 | * | 12/2019 | Norvell | A61F 15/004 |
| 2006/0155226 A1 | * | 7/2006 | Grim | A61F 13/041 602/8 |

(Continued)

FOREIGN PATENT DOCUMENTS

KR 10-0232801 B1 12/1999
KR 10-0792252 B1 1/2008

(Continued)

OTHER PUBLICATIONS

Korean Office Action (KR 10-2020-0029014), KIPO, May 19, 2020.
Korean Notice of Allowance (KR 10-2020-0029014), KIPO, Oct. 27, 2020.

*Primary Examiner* — Rachael E Bredefeld
*Assistant Examiner* — Seth R. Brown
(74) *Attorney, Agent, or Firm* — Park & Associates IP Law Office

(57) ABSTRACT

Proposed is an improved cast used for covering an affected area of a patient having a fracture or dislocation or diabetic patient to keep the continuity of the affected area and the unaffected area, and to protect the affected area from external shock.

1 Claim, 18 Drawing Sheets

(56) References Cited

U.S. PATENT DOCUMENTS

2007/0276302 A1* 11/2007 Evans ...................... D04B 1/16
602/8
2014/0121627 A1* 5/2014 Lepore .............. A61F 13/00029
604/385.01
2015/0305914 A1* 10/2015 Wu .......................... A61F 5/01
602/7

FOREIGN PATENT DOCUMENTS

| KR | 10-2014-0009679 A | 1/2014 |
| KR | 10-1417682 B1 | 7/2014 |
| KR | 10-1578399 B1 | 12/2015 |
| KR | 10-2019-0074839 A | 6/2019 |
| KR | 10-2020-0013396 A | 2/2020 |

* cited by examiner

CAST FOR PROTECTING AFFECTED AREA OF PATIENT

REFERENCE TO RELATED APPLICATIONS

This application claims the priority benefit of Korean Patent Application No. 10-2020-0029014 filed on Mar. 9, 2020, the entire contents of which are incorporated herein by reference.

FIELD OF THE INVENTION

The present disclosure relates to a cast. More particularly, the present disclosure improves a cast used for covering an affected area of a patient having a fracture or dislocation to keep the continuity of the affected area and the unaffected area, and to protect the affected area from external shock.

In addition, the present disclosure is to provide a cast to protect an affected area of a diabetic patient.

In order to accomplish the above objectives, the present disclosure provides a cast including an inner cylinder and an outer cylinder. For excellent breathability, elasticity, and bulkiness, the inner cylinder may be formed of a braided fiber. The braided fiber may be formed by braiding a draw textured yarn (DTY) and a spandex yarn at a predetermined ratio to form a fiber which has a thickness of 700 to 1000 denier, and the fiber is knitted to form a cylindrical body having a porous mesh fabric, then the cylindrical body is transformed to a double cylindrical body in which an inner skin and an outer skin are overlapped, and a divided insert portion is formed on a distal opening portion of the double cylindrical body. For excellent breathability, elasticity, and bulkiness, the outer cylinder may be formed of a braided fiber. The braided fiber of the outer cylinder may be formed by braiding a DTY and a spandex yarn at a predetermined ratio to form a fiber which has a thickness of 1400 to 4000 denier, and the fiber is knitted to form a cylindrical body having a porous mesh fabric and the cylindrical body is partially incised on a distal opening circumferential wall thereof to have split circumferential walls. Thereafter, the cylindrical body is washed and dried to facilitate impregnation of the cylindrical body with a hydraulic binder, and then impregnating the cylindrical body with the hydraulic binder is performed. The cylindrical body impregnated with the hydraulic binder is then dehumidification-packaged to prevent a hardening action of the hydraulic binder before a casting procedure for patient. When the casting procedure for a patient begins, the dehumidification package of the cylindrical body is removed, and the outer cylinder is fitted over an outer surface of the inner cylinder so that the casting procedure for the patient becomes convenient. When the outer cylinder is hardened, a structure on which breathable holes are formed is secured so that the outer cylinder protects the affected area of the patient by covering the inner cylinder, thus wearing sensation of the cast becomes cool and the cast also becomes hygienic.

In particular, in a process of knitting the cylindrical body for manufacturing the inner cylinder, partition holes each having a length of 60 to 80 cm are formed on the inner cylindrical body at regular intervals along a longitudinal direction of the inner cylindrical body, thus forming a holed cylindrical body in which an inner space thereof is divided at a region of each of the partition holes. Next, a holed double cylindrical body is formed by cutting the holed cylindrical body in a manner that upper and lower portions of the holed cylindrical body have the same length from the center of each of the partition holes, and a cut cylindrical body is folded in half at the partition hole such that the upper portion covers an outer surface of the lower portion, thus forming the holed double cylindrical body in which an inner skin and an outer skin are overlapped. Therefore, the inner cylinder having a divided insert portion configured to receive a thumb or a big toe is formed, where the divided insert portion is formed at one side of a distal opening portion of the holed double cylindrical body. Moreover, the circumferential wall of the distal opening portion of the cylindrical body for the outer cylinder is partially incised to form split circumferential walls on opposite sides from the center of the incision portions, so that a protective structure is formed on the divided insert portion of the inner cylinder and on an outer surface of the distal opening portion of the inner cylinder by covering them with the outer cylinder.

In addition, the hydraulic binder used in the outer cylinder is selected from polypropylene polyol diphenylmethanediisocyanate prepolymer, so that the outer cylinder harmless to a human body may be formed.

Therefore, the cast with excellent firmness and breathability, capable of releasing stuffiness, allowing the affected area to be observed from the outside, and comfortable at a thumb or a big toe portion may be achieved. When using the cast of the present disclosure, the cast is covered on an affected area with the inner cylinder first, then the dehumidification package of the outer cylinder is removed, and the outer surface of the inner cylinder is covered with the outer cylinder, and then the shape of the outer cylinder is molded by touching the surface of the outer cylinder to become the same shape as that of the affected area before the outer cylinder is completely hardened. By completing this process, the outer cylinder covers the outer surface of the inner cylinder and forms a mesh fabric structure when the outer cylinder is molded and hardened, then the inner surface of the hardened outer cylinder is attached to the outer skin of the inner cylinder, and then the inner skin of the inner cylinder is in contact with the affected area of a patient, so that the cast that protects the affected area is completely formed.

BACKGROUND OF THE INVENTION

A conventional cast for a patient having a fracture is processed by winding and fixing a cotton bandage over a stocking pad. This cast blocks the breathability between the cast and the affected area of the patient, which may lead to itchiness, odor, stuffiness, and unsanitary discomfort, and there is another problem with the inconvenience of constructing the cast.

To solve these problems, a method in that a skin protective cotton yarn is worn in the same way as wearing a stocking, and a hardening cotton yarn on which a hardening liquid is impregnated and which is weaved to have a porous structure is worn on the skin protective cotton yarn has been developed and applied.

Korean Patent Application No. 10-1997-0046527 entitled "cast and casting method" proposes a method of securing breathability and a simple convenient procedure performed with the method, Korean Patent Application No. 10-2006-0092355 entitled "cast for medical and skin protection" proposes an improved structure of a cast, but this case only proposed the same procedure method as conventional methods, and Korean Patent Application No. 10-2013-0134629 entitled "medical cast" specializes a type and a structure of a skin protective cotton yarn and a hardening cotton yarn, and it is registered.

However, since these methods attempt to secure the bulky characteristics of the hardening cotton yarn during a manufacturing process thereof in order to secure the breathability of the affected area of a patient after the procedure that may be a cause of pain and dissatisfaction of the patient when the breathability is not properly secured, but there are no specific plans for provision of specific method of securing the breathability of the cotton yarn in manufacturing except for changing the material of the fiber, so that there is also a problem in that uniform impregnation does not occur well when the impregnation of a hardening liquid is processed during a manufacturing process of the hardening cotton yarn. Moreover, excessive use of the hardening liquid may cause adhesion of a hand of a casting procedure operating person to an outer skin of a cast due to the sticking of the hardening liquid on the hand. In addition, a part of a hardening portion may generate a high temperature of heat so that the breathable hole may be blocked then poor breathability may occur, residual hardening liquid unnecessarily reacts after the casting procedure due to a poor hardening action since non-uniform impregnation of the hardening liquid may induce the hardening action to react only on the outer surface of the cotton yarn, and the leakage of the hardening liquid may occur so that the leakage may burn clothes or skin.

DOCUMENTS OF RELATED ART

Patent Documents (Patent Document 1) Korean Patent No. 10-0792252
(Patent Document 2) Korean Patent No. 10-1417682

SUMMARY OF THE INVENTION

The present disclosure has been made in view of the problems occurring in the related art, and an objective of the present disclosure is to provide a cast in which an outer cylinder and an inner cylinder are improved, and the cast safely protects an affected area of a patient and is easy to manufacture it. The outer cylinder is formed to harden with a minimum amount of hardening liquid so that the breathability is secured and the affected area of a patient is observed from the outside by forming a durable structure when the outer cylinder covers an outer surface of the inner cylinder. The inner cylinder has excellent breathability and elasticity, bulkiness, and excellent ability to be combined with the outer cylinder, and has a divided insert portion configured to receive a thumb or a big toe, so that a casting procedure for a finger or a foot may be performed conveniently. In addition, the outer cylinder is formed to have incision portions on a circumferential wall of a distal opening portion of the outer cylinder so that split circumferential walls are formed. Therefore, when the split circumferential walls of the outer cylinder cover the inner cylinder and are hardened, a protective structure is formed on the divided insert portion of the inner cylinder and on an outer surface of the distal opening portion of the inner cylinder.

The cast of the present disclosure includes the inner cylinder and the outer cylinder. The inner cylinder that is to be placed on the affected area of a patient is configured to have a double cylindrical body so that elasticity and breathability are secured, and has a divided insert portion configured to receive a thumb or a big toe, the divided insert portion being formed at one side of a distal opening portion of the holed double cylindrical body. The outer cylinder, which is to cover the outer surface of the inner cylinder, is configured as a breathable cylindrical body, is molded to have the same shape of the affected area by the impregnated hydraulic binder, secures the breathability and capability of being observed from the outside by forming a breathable structure when the outer cylinder is hardened, and forms a split circumferential walls on the circumferential wall of the distal opening portion of the outer cylinder by incising the distal opening portion of the outer cylinder so that the protective structure is formed on the distal opening portion of the inner cylinder and on the outer circumferential wall of the divided insert portion of the inner cylinder.

The outer cylinder of the present disclosure is formed of a braided fiber. The braided fiber is formed by braiding a draw textured yarn (DTY) and a spandex yarn at a ratio of 4:1 to 12:1 to form a fiber which has a thickness of 1400 to 4000 denier. The DTY of the outer cylinder is formed by braiding filament-yarns of a polyester fiber or a polypropylene fiber, which is a synthetic fiber, to form a set of yarns having a predetermined thickness, and applying pressure to the set of yarns at points of 0.8 to 1 cm intervals along a longitudinal direction of the set of yarns, thereby spot-joining the set of yarns. The spandex yarn of the outer cylinder is formed by placing a polyurethane fiber of 70 to 140 denier at the center position and covering a polypropylene fiber of 75 to 150 denier in a coil-type on a surface of the polyurethane fiber to form the spandex yarn of 145 to 290 denier.

By supplying the fiber to the needles before and after the knitting part of a flat-knitting machine to knit a cylindrical shape with a porous mesh fabric, a cylindrical body with excellent breathability, elasticity, and bulkiness is formed. The cylindrical body is knitted to be good at impregnation, then the cylindrical body is washed by immersing the cylindrical body in a cleaning liquid so that a foreign substance and a lubricating oil which is applied on a surface of the fiber for knitting the cylindrical body are removed, then the cylindrical body is dried by picking up the cylindrical body so that fabrics of the knitted textiles of the cylindrical body are shrunk so that the cylindrical body with elasticity is obtained, then the cylindrical body is impregnated with a hydraulic binder and is dehumidification-packaged for preventing a hardening before a casting procedure for patient, thus preparing the outer cylinder for the casting procedure.

The hydraulic binder used in the present disclosure includes polypropylene polyol diphenylmethanediisocyanate prepolymer (94 to 96 weight %) and additives (4 to 6 weight %), so that the hydraulic binder with an excellent hardening action even in small amounts and harmless to a human body is selected.

Moreover, the circumferential wall of the distal opening portion of the cylindrical body for the outer cylinder is partially incised to form the split circumferential walls on opposite sides from the center of the incision portions, so that a protective structure may be formed when the split circumferential walls cover the distal opening portion of the inner cylinder and the outer surface of the divided insert portion of the inner cylinder.

The inner cylinder of the present disclosure is formed of a braided fiber. The braided fiber is formed by braiding a DTY and a spandex yarn at a predetermined ratio to form a fiber which has a thickness of 700 to 1000 denier. The DTY of the inner cylinder is formed by braiding a filament-yarns of a polyester fiber or a polypropylene fiber, which is a synthetic fiber, to form a set of yarns having a predetermined thickness, and applying pressure to the set of yarns at points of 0.8 to 1 cm intervals along a longitudinal direction of the set of yarns, thereby spot joining the set of yarns. The spandex yarn of the inner cylinder is formed by placing a polyurethane fiber of 70 to 140 denier at the center position and covering a polypropylene fiber of 75 to 150 denier in a coil-type on a surface of the polyurethane fiber to form the spandex yarn of 145 to 290 denier. The inner cylinder is formed by supplying the braided fiber to the needles before and after the knitting part of the flat-knitting machine to knit a cylindrical body which is excellent in terms of breathability, elasticity, and bulkiness by forming the cylindrical body to have a porous mesh fabric, then the cylindrical body is cut to have a predetermined length, and then the cut cylindrical body is folded in half to form a double cylindrical body in which an inner skin and an outer skin are overlapped.

In particular, in a process of knitting the cylindrical body for manufacturing the inner cylinder, partition holes each having a length of 60 to 80 cm are formed on the inner cylindrical body at regular intervals along a longitudinal direction of the cylindrical body, thus forming a holed cylindrical body in which an inner space thereof is divided. Next, a holed double cylindrical body is formed by cutting the holed cylindrical body in a manner that upper and lower portions have the same length from a center of each of the partition holes then folding a cut cylindrical body in half at the partition hole such that the upper portion covers an outer surface of the lower portion, thus forming the holed double cylindrical body in which the inner skin and the outer skin are overlapped. Therefore, the inner cylinder having a divided insert portion configured to receive a thumb or a big toe is formed, where the divided insert portion is formed at one side of a distal opening portion of the holed double cylindrical body.

The present disclosure has advantages of breathability, elasticity, and bulkiness. More particularly, the excellent bulkiness is achieved by braiding a DTY and a spandex yarn at a ratio of 4:1 to 12:1 to form a fiber which has a thickness of 1400 to 4000 denier, where the DTY of the outer cylinder is formed by braiding filament-yarns of a polyester fiber or a polypropylene fiber, which is a synthetic fiber, to form a set of yarns having a predetermined thickness, and applying pressure to the set of yarns at points of 0.8 to 1 cm intervals along a longitudinal direction of the set of yarns, thereby spot-joining the set of yarns. Moreover, breathability and elasticity are also achieved since the fabric of the cylindrical body is knitted to be a porous mesh fabric. The elasticity is achieved since the mesh fabric of the cylindrical body is shrunk in a process of drying after the knitted cylindrical body is washed to remove the foreign substance of the knitted cylindrical body, and the hardening liquid may be uniformly impregnated between the fibers when the hydraulic binder is applied. Therefore, when the dehumidification package is removed and the casting procedure of molding a shape of the outer cylinder by touching with a hand and applying a pressure begins, then the outer shape is molded to a shape corresponding to the affected area so that a hole of mesh fabric is enlarged, then a breathable hole is secured so that the excellent breathability is achieved since a mesh fabric structure is formed when the outer cylinder is hardened. Moreover, the structural stability is secured so that the outer cylinder with a solid bracing property is established and the protection of the affected area is performed perfectively. In addition, it is possible to observe the affected area from the outside via the breathable hole is capable so that the observation of the affected area is convenient, the light in weight may be achieved, and easy to assemble to the inner cylinder and easy to process a casting procedure may be achieved.

In particular, the outer cylinder of the present disclosure uses a hydraulic binder that includes a mixture of polypropylene polyol diphenylmethanediisocyanate prepolymer and additives. Therefore, the hydraulic binder is not only harmless to a human body but also easily impregnated between the fibers which construct the outer cylinder thus combining the filament-yarn. Therefore, there are advantages of forming a strong structure by improving the hardening durability, forming and outer cylinder which is lightweight due to a porous mesh fabric thereof, and forming a protective structure by forming incision portions on the circumferential wall of the distal opening portion of the outer cylinder then forming split circumferential walls on opposite sides from the center of the incision portions so that the split circumferential walls cover the distal opening portion of the inner cylinder and the divided insert portion of the inner cylinder.

Meanwhile, the inner cylinder of the present disclosure is formed of a braided fiber. The braided fiber is formed by braiding a DTY and a spandex yarn at a predetermined ratio to form a fiber which has a thickness of 700 to 1000 denier, so that there are advantages of excellent breathability, elasticity, and bulkiness due to a porous mesh structure, and excellent at flexibility and breathability due to a double cylindrical structure in which the inner skin and the outer skin thereof are overlapped so that the structure does not burden the affected area, does not cause stuffiness, and has a high absorption rate. The DTY of the inner cylinder is formed by braiding filament-yarns of a polyester fiber or a polypropylene fiber, which is a synthetic fiber, to form a set of yarns having a predetermined thickness, and applying pressure to the set of yarns at points of 0.8 to 1.0 cm intervals along a longitudinal direction of the set of yarns, thereby spot-joining the set of yarns. The spandex yarn of the inner cylinder is formed by placing a polyurethane fiber of 70 to 140 denier at the center position and covering a polypropylene fiber of 75 to 150 denier in a coil-type on a surface of the polyurethane fiber to form the spandex yarn of 145 to 290 denier.

In particular, in a process of knitting the cylindrical body for manufacturing the inner cylinder, partition holes each having a length of 60 to 80 cm are formed on the inner cylindrical body at regular intervals along a longitudinal direction of the cylindrical body, thus forming a holed cylindrical body. Next, a holed double cylindrical body is formed by cutting the holed cylindrical body in a manner that upper and lower portions of the holed cylindrical body have the same length from a center of each of the partition holes, then folding the cut cylindrical body in half at the partition hole such that the upper portion covers an outer surface of the lower portion, thus forming the holed double cylindrical body in which an inner skin and outer skin are overlapped. Therefore, a divided insert portion configured to receive a thumb or a big toe is formed, where the divided insert portion is formed at one side of the distal opening portion of the holed double cylindrical body, so that the inner cylinder without processing an additional preparation to form a divided insert portion may be achieved. Therefore, a casting procedure for finger or foot may be performed easily. Moreover, the circumferential wall of the distal opening portion of the outer cylinder is partially incised so that split circumferential walls are formed on opposite sides from the center of the incision portions, so that a protective structure is formed on the divided insert portion of the inner cylinder and on an outer surface of the distal opening portion of the inner cylinder by covering on thereof with the outer cylinder.

In addition, the inner cylinder is exposed to the upper and lower portion thereof to the external side of the upper end and the lower end portion of the outer cylinder, respectively, and the exposed portions cover and attach the outer surface of the outer cylinder. Therefore, there is an advantage of do not have to prepare the extra attaching method since the outer cylinder becomes integrated with the inner cylinder when the outer cylinder is hardened. At this time, the outer skin of the inner cylinder is in contact with the inner skin of the outer cylinder, and a breathable space is formed between the outer skin and the inner skin of the inner cylinder so that the air-communication becomes smooth, and also the stuffiness sensation caused by the cast may be prevented.

DETAILED DESCRIPTION OF THE INVENTION

Figure 1A:
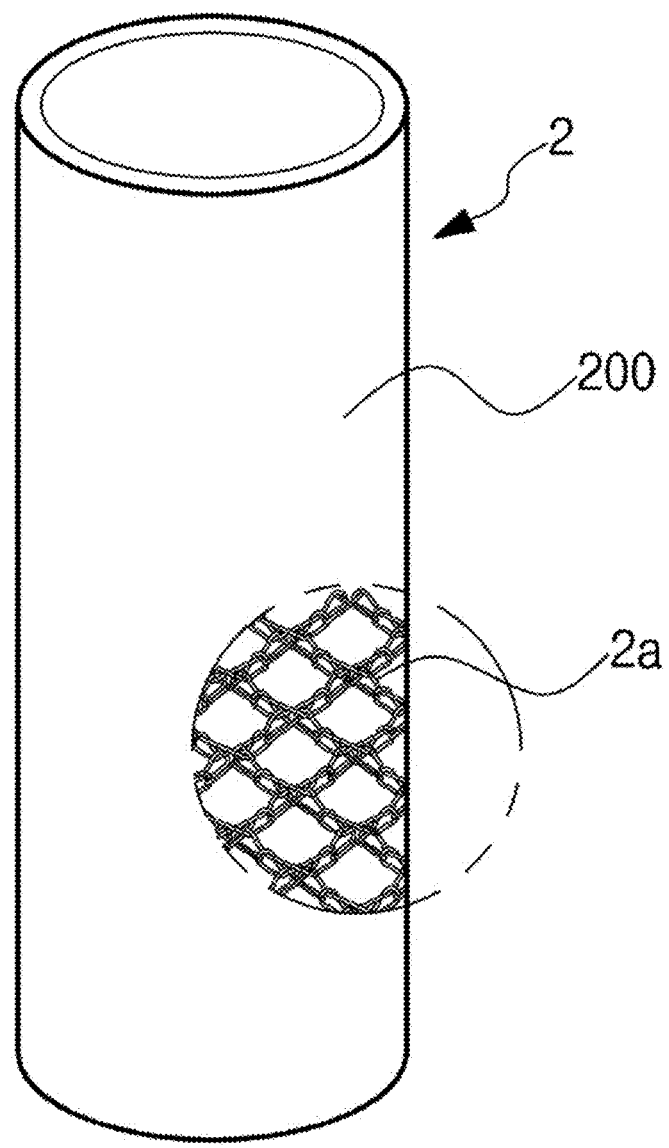
FIG. 1A is a view illustrating a construction of an outer cylindrical body of the present disclosure.
Figure 1B:
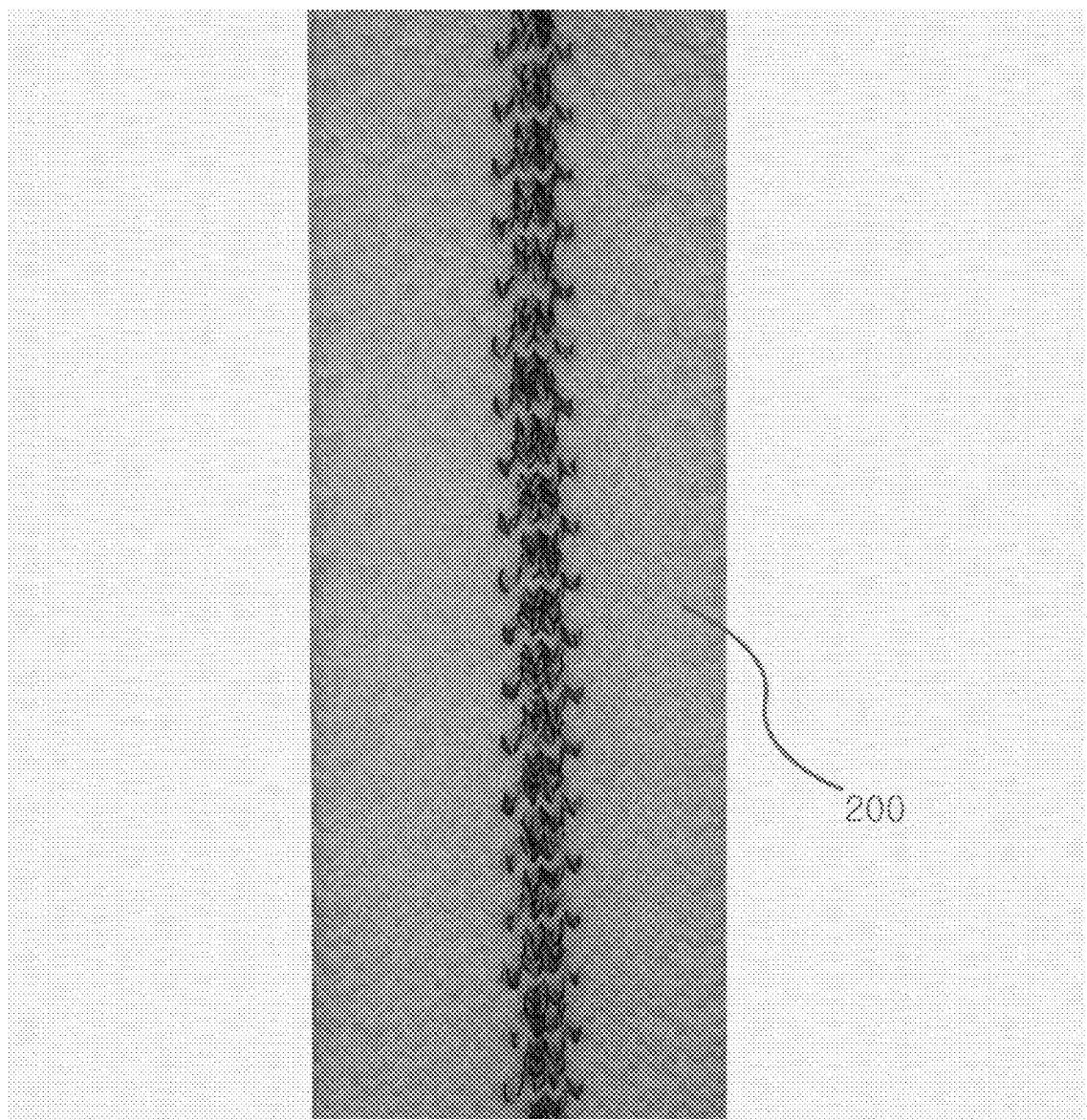
FIG. 1B is an actual picture of FIG. 1A.
Figure 1C:
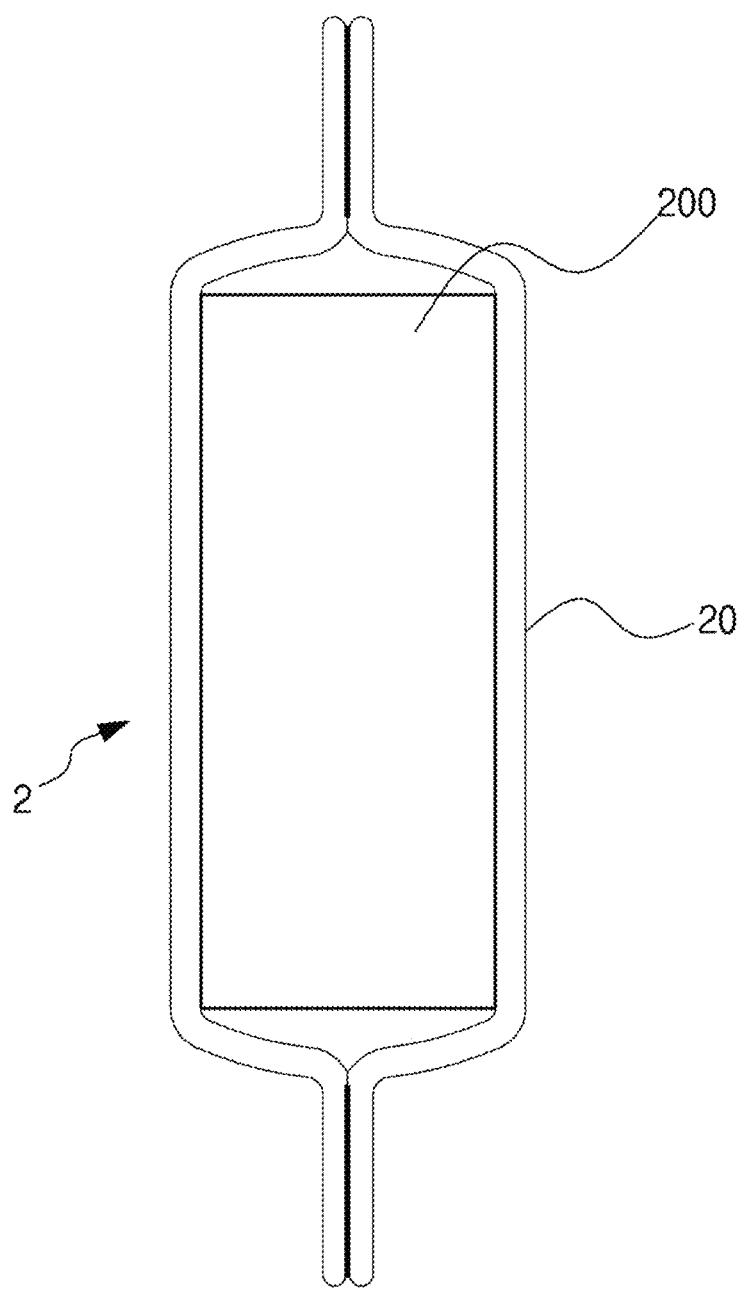
FIG. 1C is a view illustrating a dehumidification packaging of the outer cylindrical body of FIG. 1A.
Figure 2A:
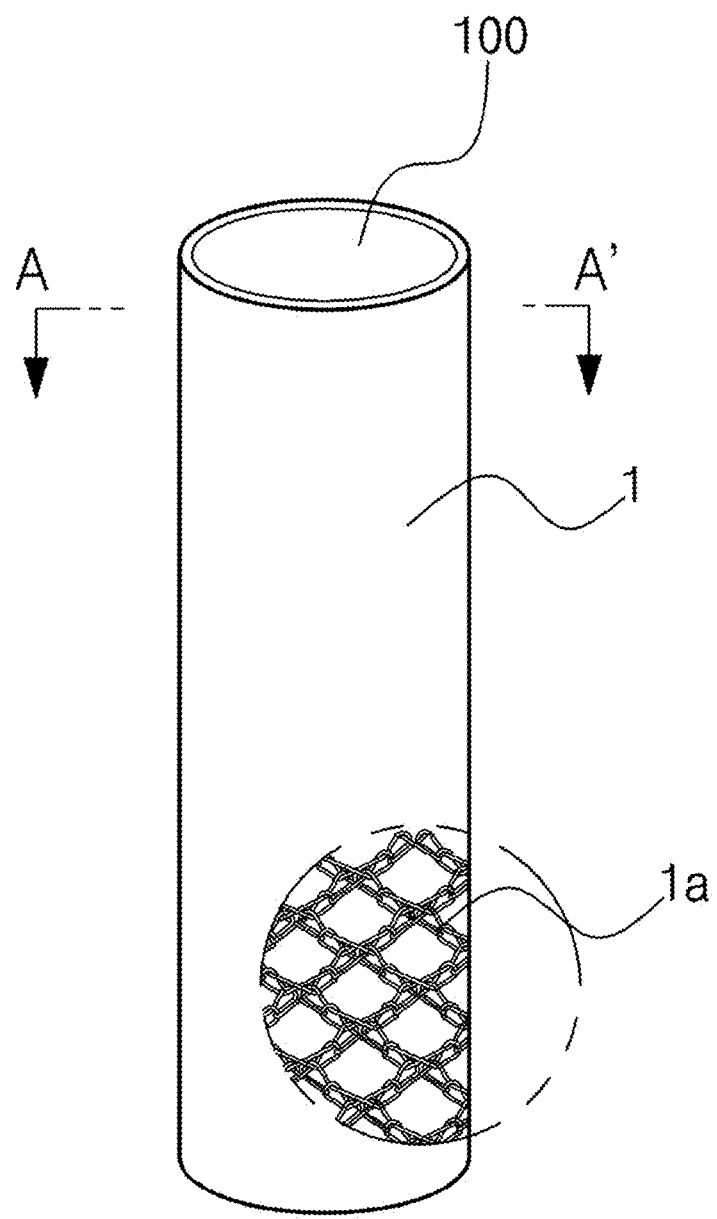
FIG. 2A is a view illustrating a construction of an inner cylindrical body of the present disclosure.
Figure 2B:
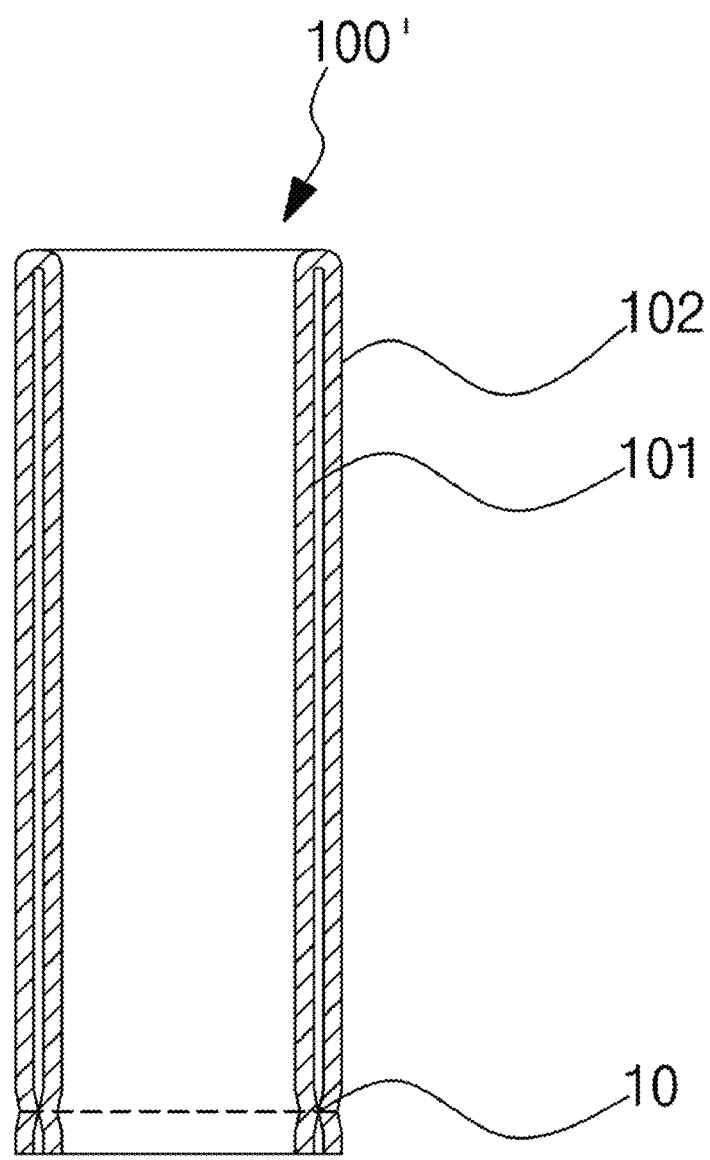
FIG. 2B is a sectional view taken along line A-A' of FIG. 2A.
Figure 3A:
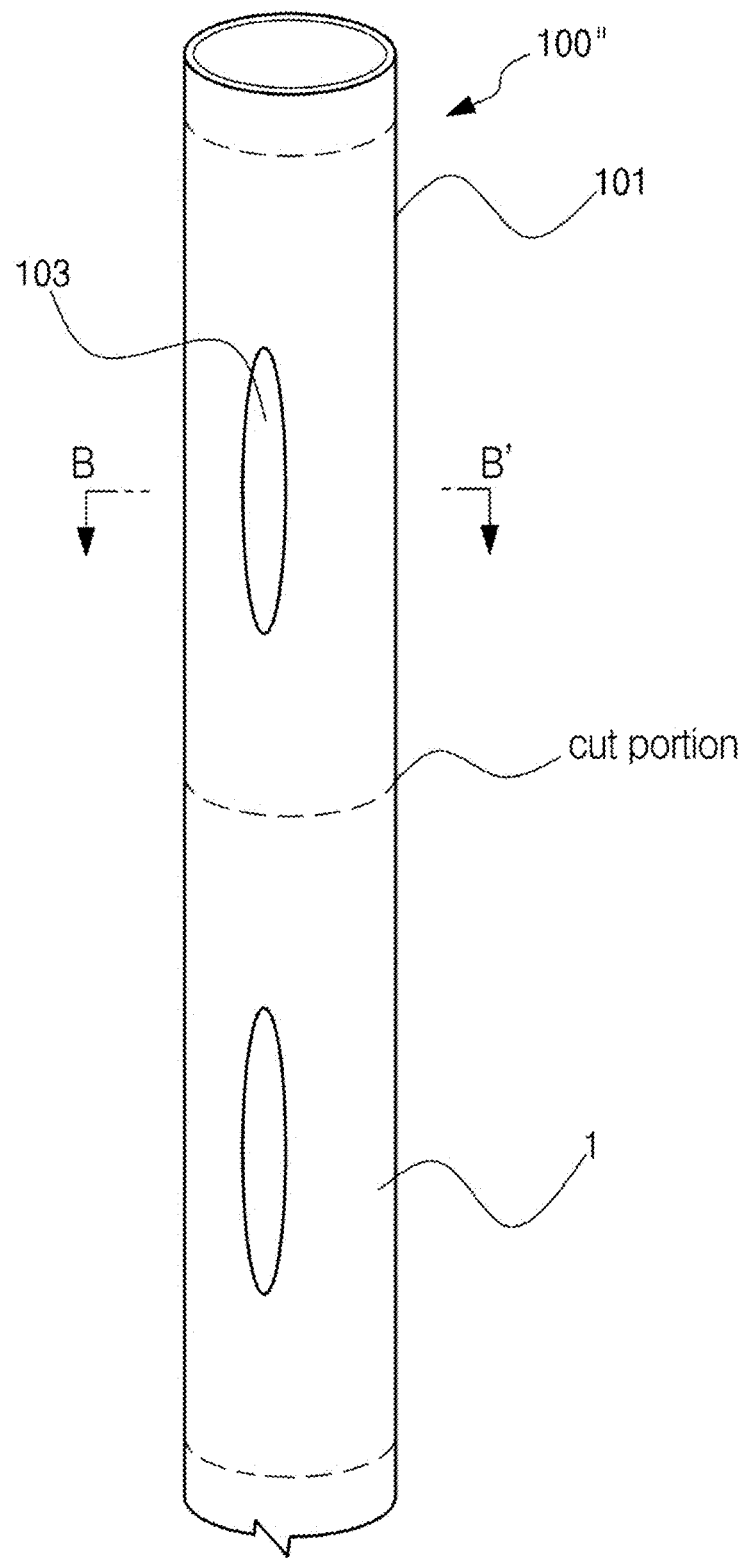
FIG. 3A is a view illustrating a holed cylindrical body of the present disclosure.
Figure 3B:
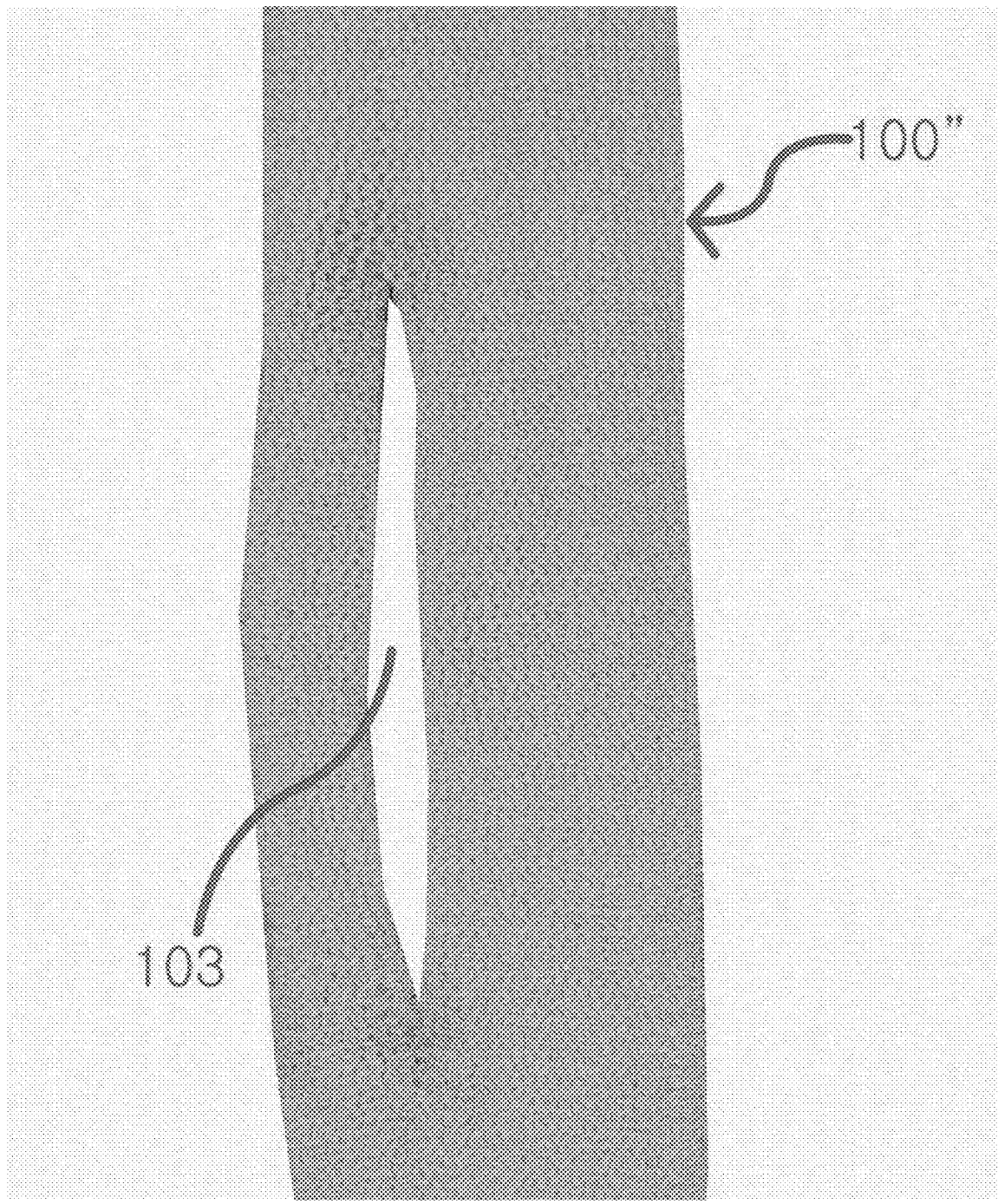
FIG. 3B is an actual picture of FIG. 3A.
Figure 3C:
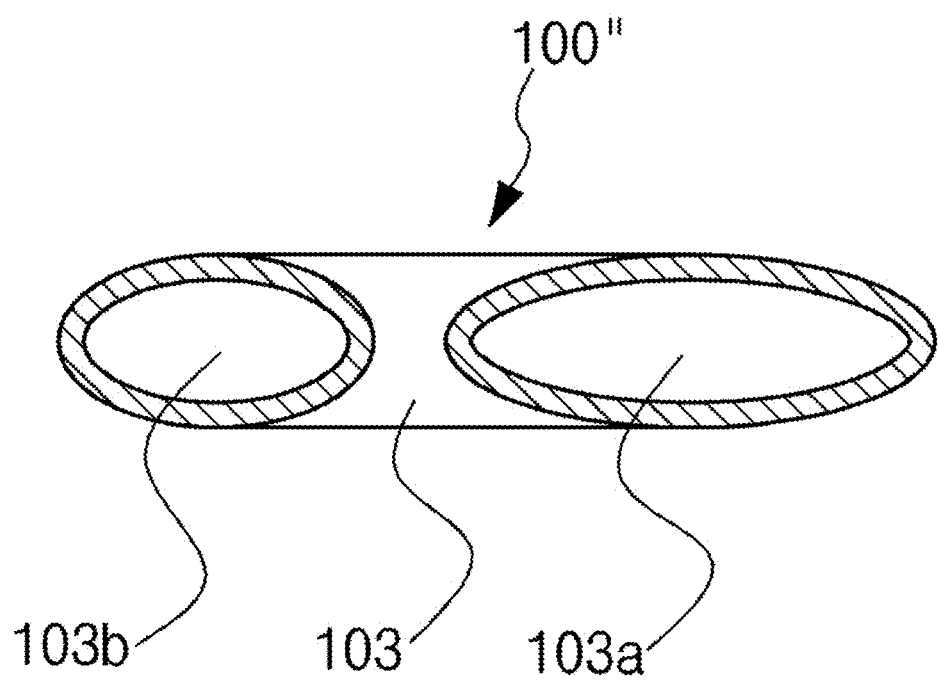
FIG. 3C is a sectional view taken along line B-B' of FIG. 3A.
Figure 3D:
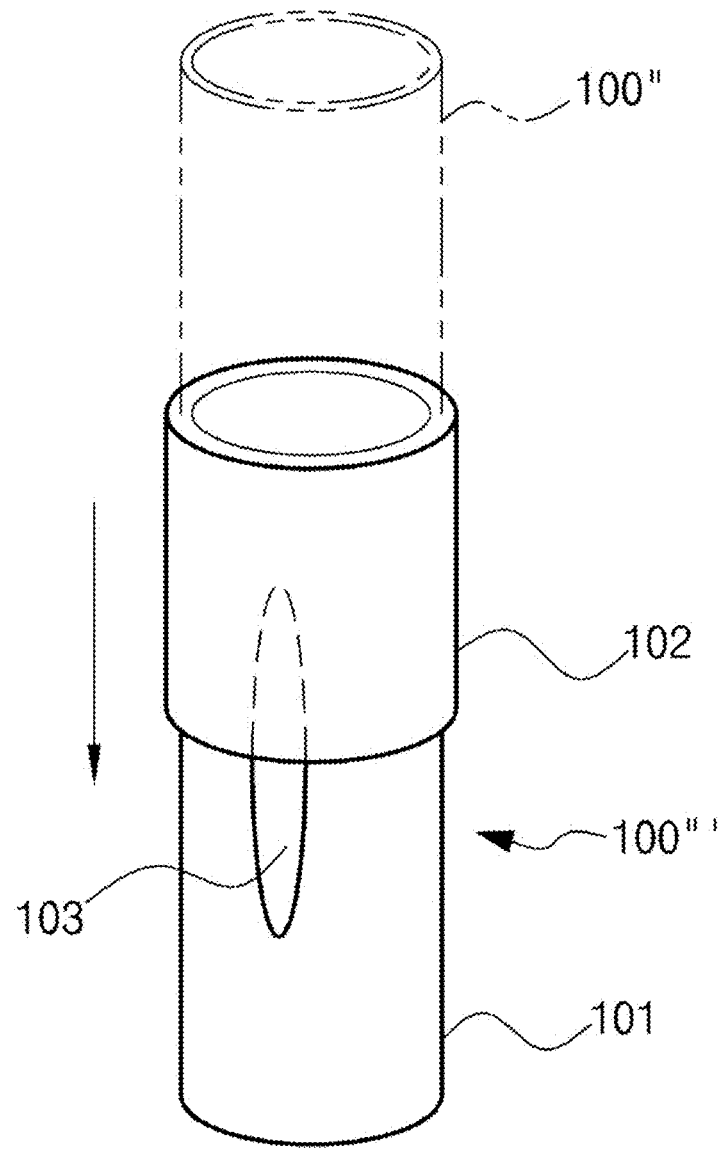
FIG. 3D is a view illustrating a process for making a holed double cylindrical body by folding the holed cylindrical body in half.
Figure 3E:
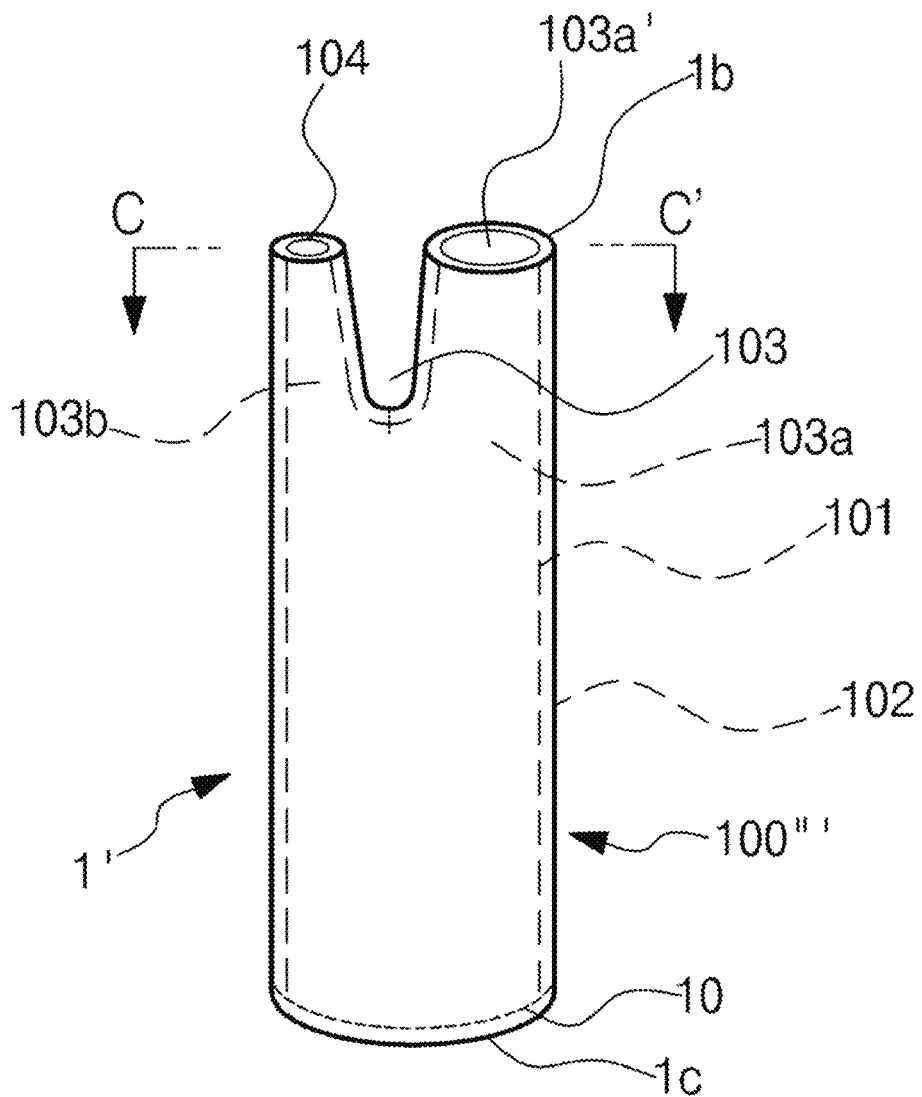
FIG. 3E is a view illustrating the inner cylinder in which a divided insertion portion is formed.
Figure 3F:
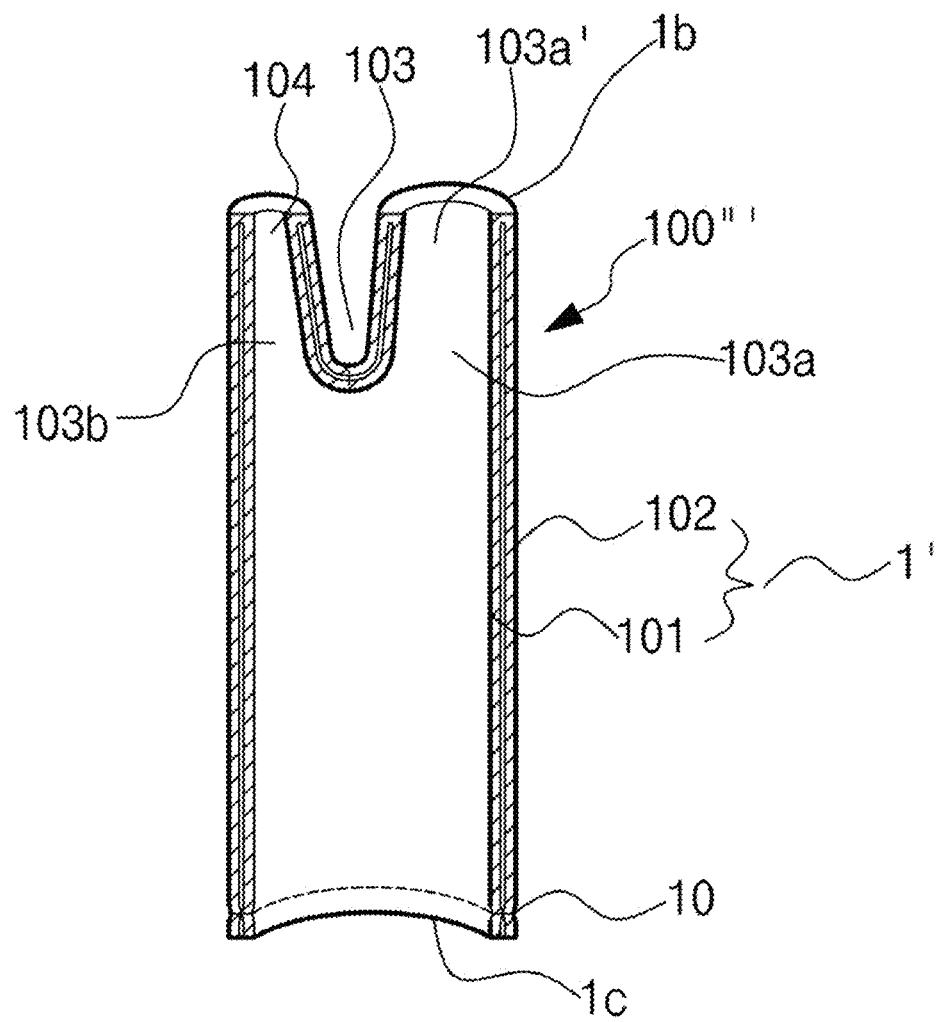
FIG. 3F is an actual picture of FIG. 3E.
Figure 3G:
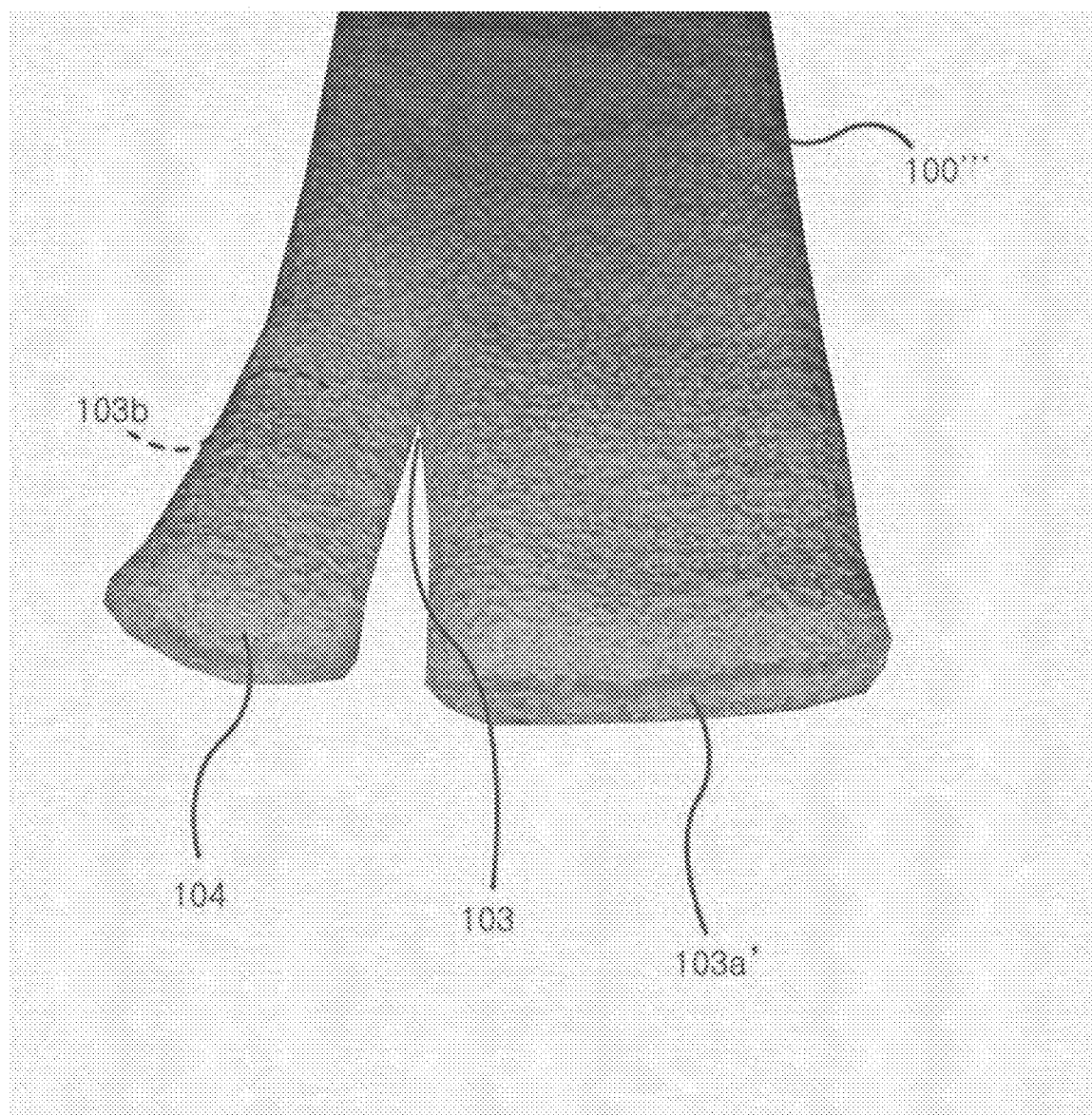
FIG. 3G is an enlarged picture of the divided insertion portion.
Figure 3H:
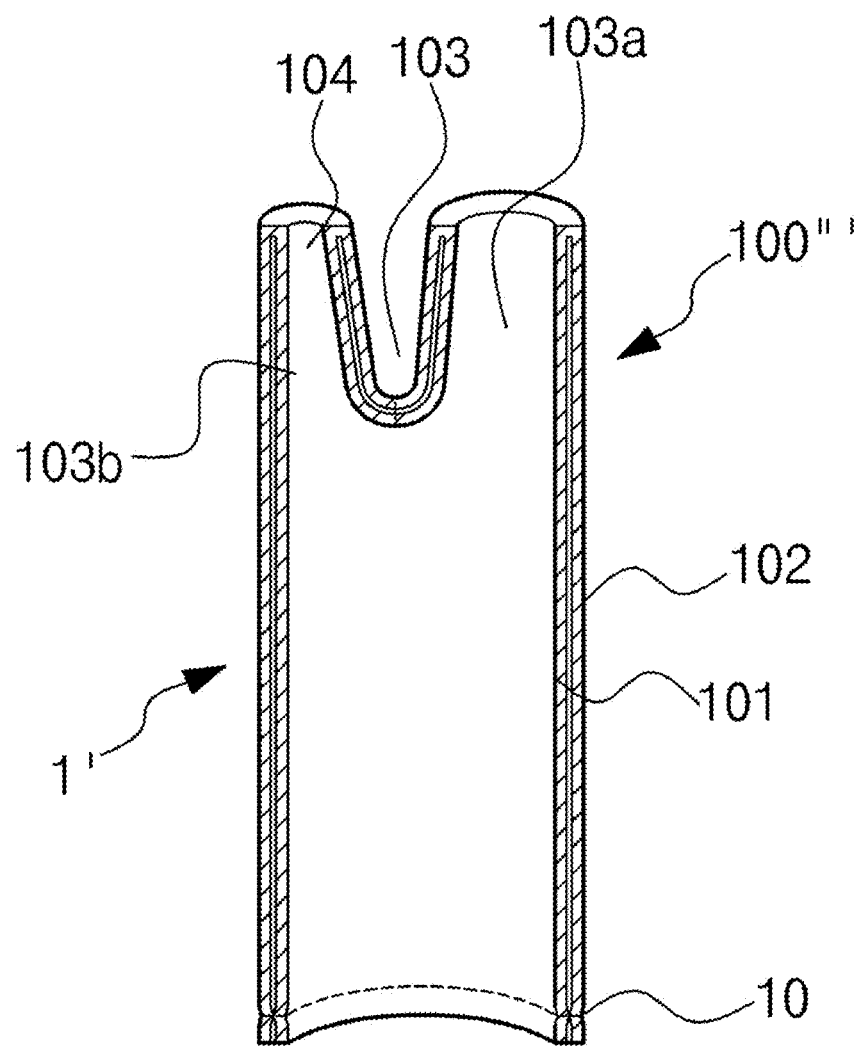
FIG. 3H is a sectional view taken along line C-C' of FIG. 3E.
Figure 4A:
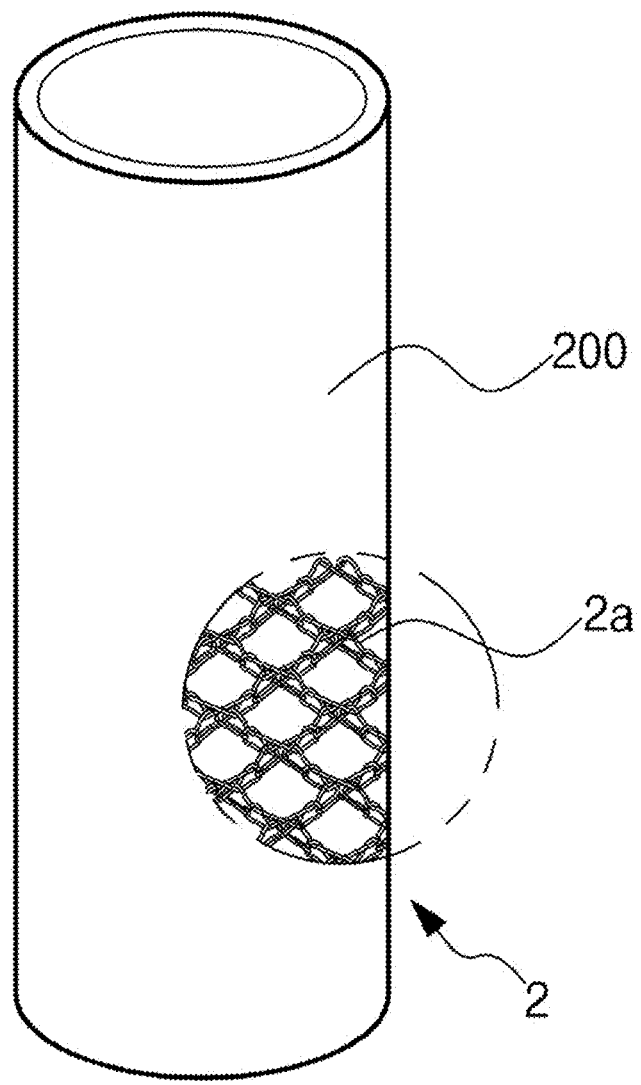
FIGS. 4A, 4B, and 4C are views illustrating a process where the circumferential wall of a distal opening of the outer cylindrical body is incised and split circumferential walls are formed, and the protective structure is formed.
Figure 4B:
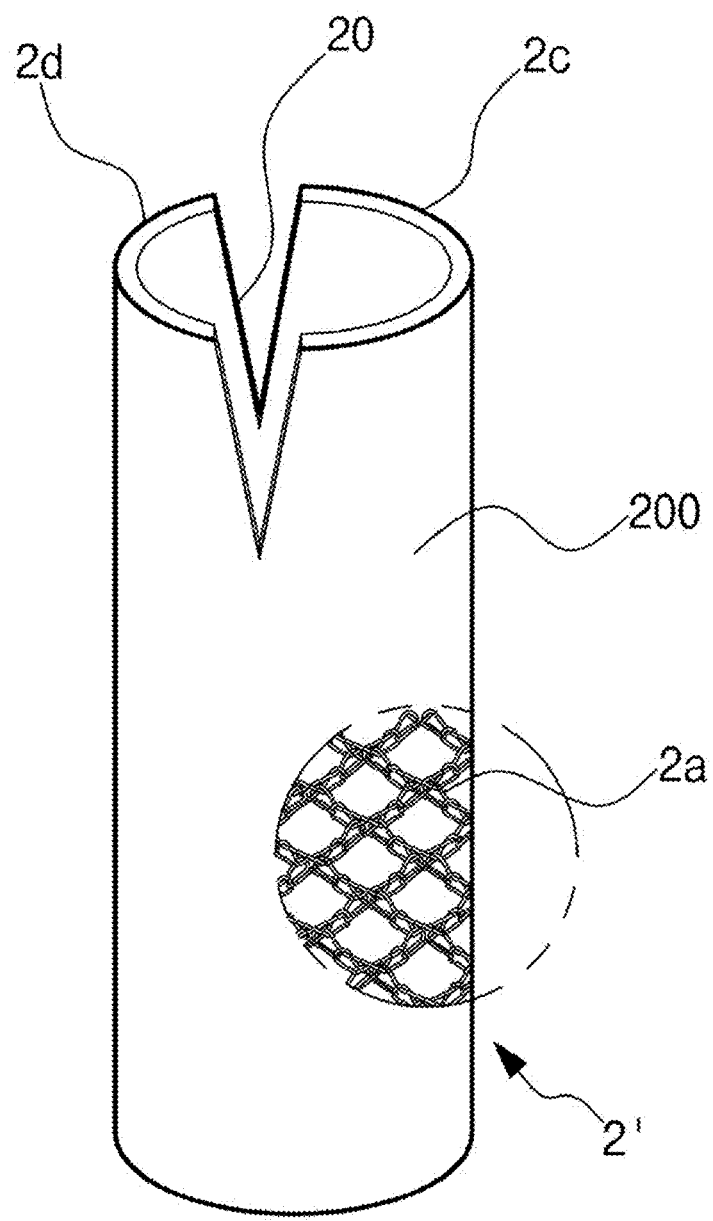
Figure 4C:
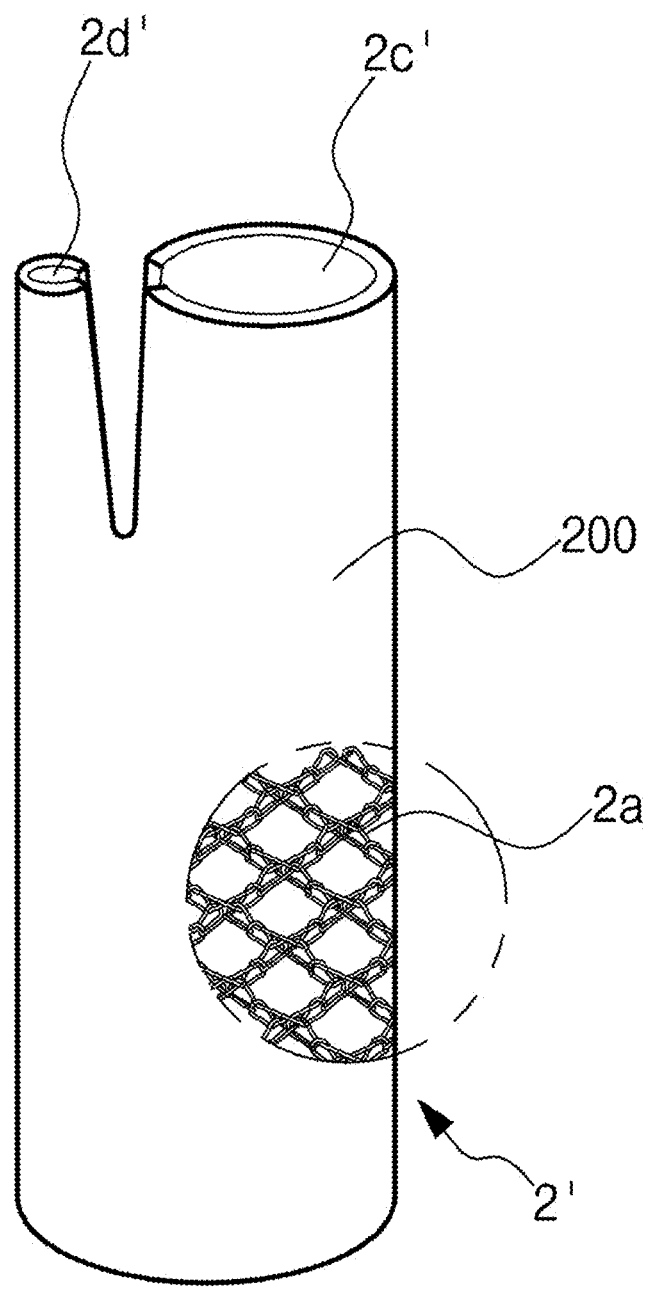

The present disclosure includes an inner cylinder 1 and an outer cylinder 2. The inner cylinder 1 has a double cylindrical body 100' and is placed on an affected area requiring a cast. The outer cylinder 2 has a diameter larger than that of the inner cylinder 1 to cover the inner cylinder 1 and formed of a cylindrical body with breathability, is molded in a shape of the affected area by impregnating the cylindrical body with a hydraulic binder which is for hardening the outer cylinder 2 to the molded shape, thus forming a breathable structure to protect an outer circumferential wall of the inner cylinder 1 when the outer cylinder 2 is hardened, and has a capability of being observed from the outside.

The outer cylinder 2 is formed of a braided fiber. The braided fiber is formed by braiding a draw texturing yarn (DTY) and a spandex yarn at a ratio of 4:1 to 12:1 to form a fiber which has a thickness of 1400 to 4000 denier. The DTY of the outer cylinder 2 is formed by braiding filament-yarns of a polyester fiber or a polypropylene fiber, which is a synthetic fiber, to form a set of yarns having a predetermined thickness, and applying pressure to the set of yarns at points of 0.8 to 1 cm intervals along a longitudinal direction of the set of yarns, thereby spot-joining the set of yarns. The spandex yarn of the outer cylinder 2 is formed by placing a polyurethane fiber of 70 to 140 denier at the center position and covering a polypropylene fiber of 75 to 150 denier in a coil-type on a surface of the polyurethane fiber to form the spandex yarn of 145 to 290 denier.

By supplying the fibers to the needles before and after a knitting part of a flat-knitting machine to knit a cylindrical shape having a porous mesh fabric 2A, a cylindrical body 200 with excellent breathability, elasticity, and bulkiness is formed. The knitted cylindrical body 200 is washed by immersing the knitted cylindrical body 200 in a cleaning liquid so that a foreign substance and a lubricating oil which is applied on a surface of the fiber for knitting the cylindrical body 200 are removed, then the knitted cylindrical body 200 is dried by picking up the cylindrical body 200 so that fabrics of the knitted textiles are shrunk so that the cylindrical body 200 with elasticity is obtained. The cylindrical body 200 is impregnated with a hydraulic binder and is dehumidification-packaged 2B by separating the hydraulic binder from air for preventing a hardening before a casting procedure for patient, thus preparing the outer cylinder 2 for the casting procedure.

The hydraulic binder used in the present disclosure includes polypropylene polyol diphenylmethanediisocyanate prepolymer (94 to 96 weight %) and additives (4 to 6 weight %). The additive includes at least one selected from a group consisting of dimorpholinodiethylether, silicone oil, and tetraethylenediamine dipropylene glycol. Therefore, the hydraulic binder which is harmless to a human body and has a stable hardening property may be realized.

Therefore, the outer cylinder 2' of the present disclosure forms incision portions 20 on a distal opening portion of the cylindrical body 200 that forms the outer cylinder 2, and forms split circumferential walls 2C, 2D on opposite sides from the center of the incision portions 20.

The inner cylinder 1 of the present disclosure is formed of a braided fiber. The fiber is formed by braiding a DTY and a spandex yarn at a predetermined ratio to form a fiber which has a thickness of 700 to 1000 denier. The DTY of the inner cylinder is formed by braiding filament-yarns of a polyester fiber or a polypropylene fiber, which is a synthetic fiber, to form a set of yarns having a predetermined thickness, and applying pressure to the set of yarns at points of 0.8 to 1 cm intervals along the longitudinal direction of the set of yarns, thereby spot-joining the set of yarns. The spandex yarn of the inner cylinder is formed by placing a polyurethane fiber of 70 to 140 denier at the center position and covering a polypropylene fiber of 75 to 150 denier in a coil-type on the surface of the polyurethane fiber to form the spandex yarn of 145 to 290 denier. By supplying the fibers to the needles before and after the knitting part of the flat-knitting machine, a cylindrical body 100 having a porous mesh fabric 1A is formed. The cylindrical body 100 is cut and the cut cylindrical body is folded in half so that a double cylindrical body 100' in which an inner skin 101 and an outer skin 102 are overlapped is formed and an end portion where the inner skin 101 and the outer skin 102 is encountered is sewed with sewing yarn 10 to form the inner cylinder 1.

In a process of knitting the inner cylindrical body, partition holes 103 each having a length of 60 to 80 cm are formed on the inner cylindrical body at regular intervals along the longitudinal direction of the cylindrical body, thus forming a holed cylindrical body 100″ in which an inner space of the cylindrical body is divided into a large space 103A and a small space 103B at a region of each of the partition holes 103. A holed double cylindrical body 100′″ is formed by cutting the holed cylindrical body 100″ in a manner that upper and lower portions of the holed cylindrical body 100″ have the same length from a center of each of the partition holes 103 and then folding the cut cylindrical body in half at the partition hole 103 such that the upper portion covers an outer surface of the lower portion, thus forming the holed double cylindrical body 100′″ in which the inner skin 101 and the outer skin 102 are overlapped is formed, and then the end portions of the inner skin 101 and the outer skin 102 are sewed with the sewing yarn 10, so that a divided insert portion 104 in which a thumb or a big toe is inserted is formed on a side of the distal opening portion 103A′ of the holed double cylindrical body 100′″.

Figure 5:
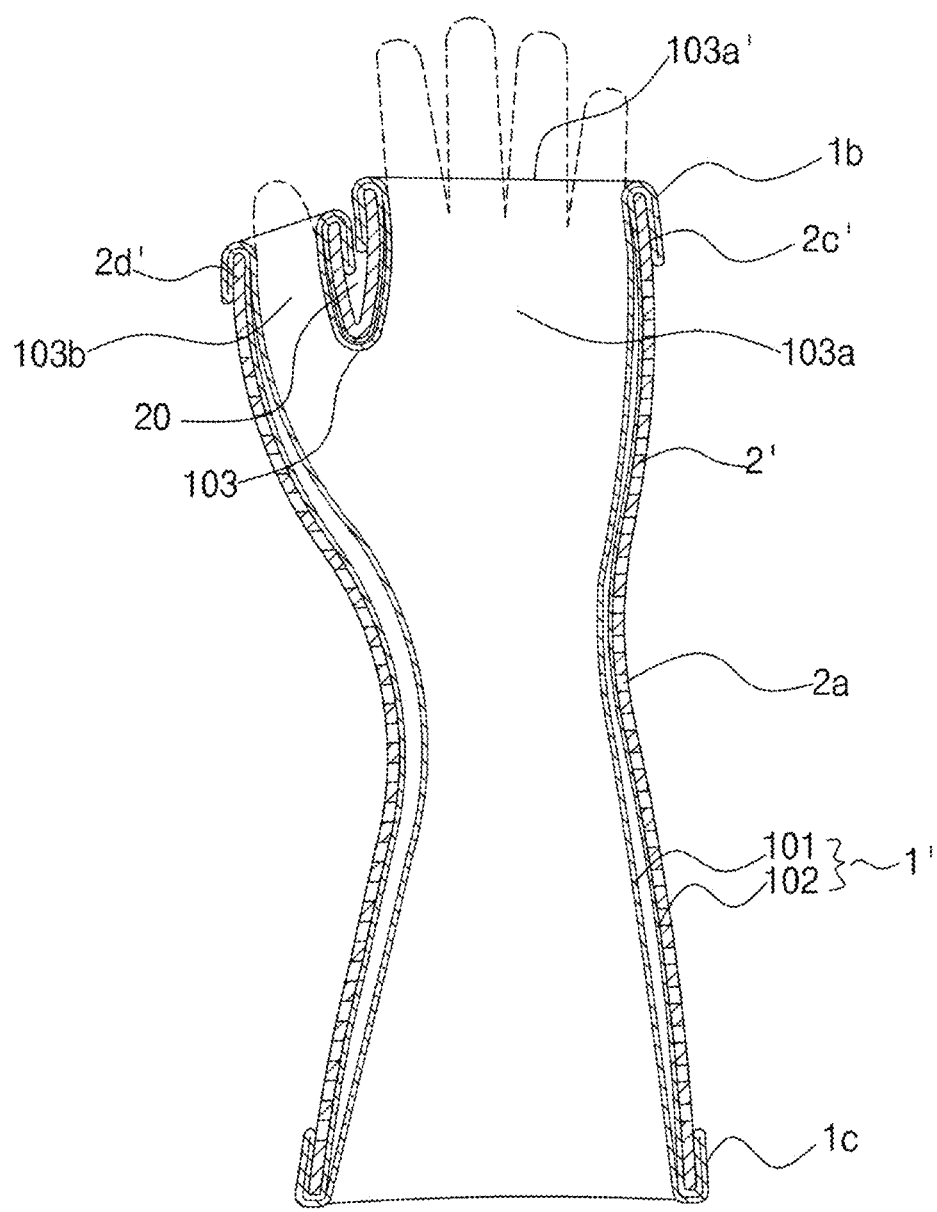
FIG. 5 is a sectional view of a cast applied on a hand.
Figure 6:
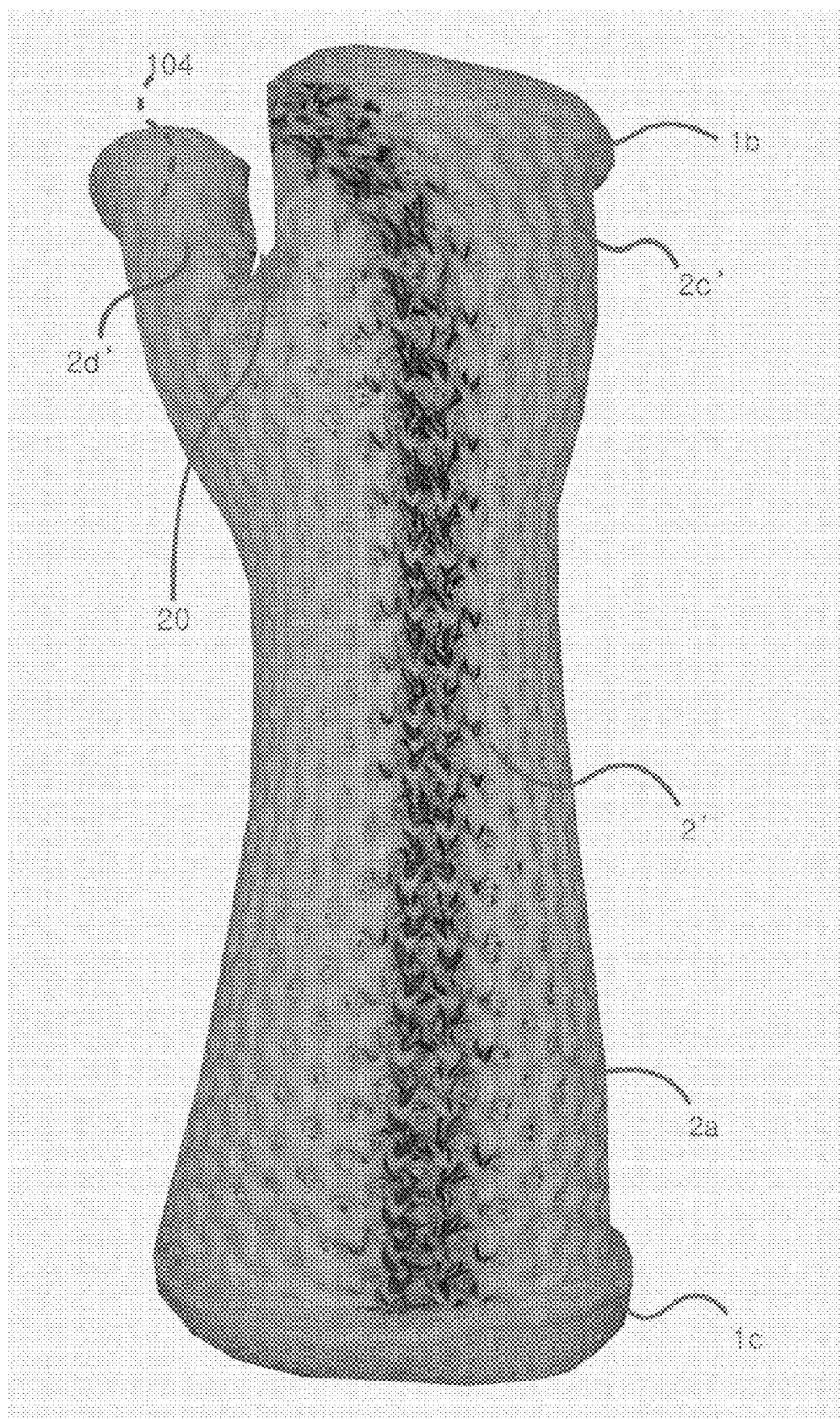
FIG. 6 is an actual picture of FIG. 5.

In addition, the inner cylinder 1′ is exposed to the upper and lower portion 1B, 1C thereof to the external side of the upper end and the lower end portion of the outer cylinder 2, respectively, so that the exposed portions cover the upper and lower portion of the outer cylinder 2′ (see FIG. 5) so that the cast which the outer cylinder 2′ and the inner cylinder 1′ are combined is formed.

At this time, the outer skin 102 of the inner cylinder 1′ is in contact with the inner surface of the outer cylinder 2′, and the inner skin 101 of the inner cylinder 1′ is in contact with the affected area of a patient.

In addition, when the inner cylinder 1′ covers the affected area and the outer cylinder 2′ is combined therewith, the protective structure is formed on the outer surface of the distal opening portion 103A′ and the divided insert portion 104 of the inner cylinder 1′ since the split circumferential walls 2C, 2D of the outer cylinder 2′ covers and is hardened on the distal opening portion 103A′ and the divided insert portion 104 of the inner cylinder 1′.

Therefore, the cast protecting the affected area, capable of releasing stuffiness due to the breathability and tactile sensation thereof, and capable of enabling the affected area to be observed from the outside is achieved by performing the proposed process of the present disclosure. The process is performed by removing the dehumidification package 2B of the outer cylinder 2′ then covering the outer surface of the inner cylinder 1′ with the outer cylinder 2′ first, then molding the shape of the outer cylinder 2′ by touching the surface of the outer cylinder 2′ to form the surface into the same shape of the affected area. By completing the process, the outer cylinder 2′ covers the outer surface of the inner cylinder 1′ with the forming a mesh fabric structure 2A when the outer cylinder is molded and hardened, then the inner surface of the hardened outer cylinder 2′ is attached to the outer skin 102 of the inner cylinder 1′, and then the inner skin 101 of the inner cylinder 1′ is contact with the affected area so that the affected area protecting cast is completely formed.

What is claimed is:

1. A cast for protecting an affected area of a patient, the cast being formed by covering an outer cylinder on an outer surface of an inner cylinder and comprising:
    the inner cylinder configured to be placed on an affected area to which the cast is to be worn, the inner cylinder being configured as a breathable double cylindrical body;
    the outer cylinder configured as a breathable cylindrical body having a diameter larger than that of the inner cylinder, the outer cylinder being covered on the outer surface of the inner cylinder, wherein the outer cylinder is impregnated with a hydraulic binder for molding a shape of the affected area and hardened to the desired shape, thus forming a breathable structure on the outer surface of the inner cylinder for protecting the affected area, and allowing the affected area to be observed from the outside through the breathable structure of the outer cylinder;
    wherein the outer cylinder is formed of a braided fiber which is formed by braiding a draw textured yarn (DTY) and a spandex yarn at a ratio of 4:1 to 12:1 to form a fiber which has a thickness of 1400 to 4000 denier, supplying the fiber to a flat-knitting machine to knit an outer cylindrical body formed with a porous mesh fabric, impregnating the outer cylindrical body with the hydraulic binder, dehumidification packaging the outer cylindrical body for preventing the hydraulic binder from being hardened before a casting procedure, and forming incision portions on a circumferential wall of a distal opening portion of the outer cylindrical body to form split circumferential walls on opposite sides of the incision portions,
    wherein the DTY of the outer cylinder is formed by braiding filament-yarns of a polyester fiber or a polypropylene fiber, which is a synthetic fiber, to form a set of yarns having a predetermined thickness, and applying pressure to the set of yarns at points of 0.8 to 1 cm intervals along a longitudinal direction of the set of yarns, thereby spot-joining the set of yarns,
    wherein the spandex yarn of the outer cylinder is formed by placing a polyurethane fiber of 70 to 140 denier and covering a polypropylene fiber of 75 to 150 denier in a coil shape on a surface of the polyurethane fiber to form the spandex yarn of 145 to 290 denier,
    wherein the inner cylinder is formed of a braided fiber which is formed by braiding a DTY and a spandex yarn at a predetermined ratio to form a fiber which has a thickness of 700 to 1000 denier, supplying the fiber to a flat-knitting machine to knit an inner cylindrical body formed with a porous mesh fabric, and forming a double cylindrical body, wherein in a process of knitting the inner cylindrical body, partition holes each having a length of 60 to 80 cm are formed on the inner cylindrical body at regular intervals along a longitudinal direction of the inner cylindrical body, thus forming a holed cylindrical body in which an inner space thereof is divided into a large space and a small space at a region of each of the partition holes,
    wherein the holed cylindrical body is cut in a manner that upper and lower portions of the holed cylindrical body have the same length from a center of each of the partition holes, and a cut cylindrical body is folded in half at the partition hole such that the upper portion covers an outer surface of the lower portion, thus forming a holed double cylindrical body in which an inner skin and an outer skin are overlapped, so that the inner cylinder having a divided insert portion configured to receive a thumb or a big toe is formed, wherein the divided insert portion is formed at one side of the distal opening portion of the holed double cylindrical body and communicates with the small space,
    wherein the DTY of the inner cylinder is formed by braiding filament-yarns of a polyester fiber or a polypropylene fiber, which is a synthetic fiber, to form a set of yarns having a predetermined thickness, and applying pressure to the set of yarns at points of 0.8 to 1 cm intervals along a longitudinal direction of the set of yarns, thereby spot-joining the set of yarns, and wherein the spandex yarn of the inner cylinder is formed by placing a polyurethane fiber of 70 to 140 denier and covering a polypropylene fiber of 75 to 150 denier in a coil shape on a surface of the polyurethane fiber to form the spandex yarn of 145 to 290 denier.

* * * * *